US006313231B1

(12) United States Patent
Hosokawa et al.

(10) Patent No.: US 6,313,231 B1
(45) Date of Patent: Nov. 6, 2001

(54) SUPERABSORBENT RESIN COMPOSITION

(75) Inventors: Yasunori Hosokawa; Tadashi Igarashi; Isao Tsuru; Yoko Hanada, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/109,402

(22) Filed: Jul. 2, 1998

(30) Foreign Application Priority Data

Jul. 3, 1997 (JP) .................................................... 9-178213

(51) Int. Cl.[7] .................................................... C08C 19/24
(52) U.S. Cl. .................... 525/340; 525/342; 525/344; 525/346; 525/364; 525/365; 525/366; 525/370; 525/372; 525/379; 525/382
(58) Field of Search ..................................... 524/417, 147; 525/340, 342, 344, 346, 364, 365, 366, 370, 372, 379, 382

(56) References Cited

U.S. PATENT DOCUMENTS

| 4,043,952 | 8/1977 | Ganslaw et al. . |
| 5,126,382 | 6/1992 | Hollenberg et al. . |
| 5,145,906 | 9/1992 | Chambers et al. . |
| 5,486,312 | * 1/1996 | Sandiford et al. ................. 252/315.1 |
| 5,629,377 | * 5/1997 | Burgert et al. ........................ 524/832 |

FOREIGN PATENT DOCUMENTS

| 0233067A2 | 8/1987 | (EP) . |
| 0621041A1 | 10/1994 | (EP) . |
| 0676420A2 | 10/1995 | (EP) . |
| 2310156 | 12/1976 | (FR) . |
| 901554 | 7/1962 | (GB) . |
| 1536035 | 12/1978 | (GB) . |
| 62-36411 | 2/1987 | (JP) . |
| 6306118 | 11/1994 | (JP) . |
| 7145326 | 6/1995 | (JP) . |
| WO9605234 | 2/1996 | (WO) . |

OTHER PUBLICATIONS

Patent Abstracts of Japan, JP 56 089838, Jul. 21, 1981 (abstract).

* cited by examiner

*Primary Examiner*—Judy M. Reddick
(74) *Attorney, Agent, or Firm*—Birch, Stewart, Kolasch & Birch, LLP

(57) ABSTRACT

A superabsorbent resin composition comprising the following components (A), (B) and (C), wherein (A) is a superabsorbent resin, (B) is a metal compound containing at least one metal A selected from the group consisting of titanium and zirconium and (C) is a chelating agent.

6 Claims, No Drawings

SUPERABSORBENT RESIN COMPOSITION

BACKGROUND OF THE INVENTION

1 Field of the Invention

The present invention relates to a superabsorbent resin composition.

2 Description of Related Art

Superabsorbent resins have been widely used as a water-absorbing material in absorbent articles in the sanitary field, such as disposable diapers for babies, adults or those suffering from incontinence, and sanitary napkins. It is known that water-soluble polymers (crosslinked polymers) constituting such superabsorbent resins undergo molecular weight reduction (degradation) and deterioration with time in the presence of radical generating species, such as hydrogen peroxide or L-ascorbic acid or a salt thereof In particular, where the superabsorbent resin is used in absorbent articles such as disposable diapers and sanitary napkins, because L-ascorbic acid or a salt thereof is present in body fluids, such as urine, blood, and perspiration, it has been a serious problem that a superabsorbent resin used in such absorbent articles undergoes degradation and deterioration with time due to the radicals generated from L-ascorbic acid or a salt thereof and reduces its capacity of retaining a body fluid.

The degradation reaction of a water-soluble polymer due to such radical generating species is conspicuous after the polymer has absorbed an aqueous liquid or a body fluid, such as urine, blood or perspiration (hereinafter referred to as a water-containing condition), especially in the co-presence of transition metal ions capable of having more than one oxidation number, such as iron ions or copper ions, in the air.

Known approaches for inhibiting the above-described degradation and deterioration of superabsorbent resins include (1) a method comprising sealing the superabsorbent resin under reduced pressure, or in a nitrogen atmosphere so as to avoid contact with air (especially oxygen), (2) a method comprising using highly purified water or raw materials so as to prevent metallic ions from entering the superabsorbent resin, (3) a method comprising adding an antioxidant or a reducing agent to the superabsorbent resin, (4) a method of adding proteins or enzymes to the superabsorbent resin, and (5) a method of adding to the superabsorbent resin, metal chelating agents, such as citric acid, (poly)phosphoric acid or a salt thereof, and ethylenediaminetetraacetic acid (EDTA) or a salt thereof.

However, the methods (1) and (2) are in many cases practically impossible to apply depending on the use of the superabsorbent resin. Methods (3), (4), and (5) that rely on conventional additives achieve some effect in suppressing degradation and deterioration of superabsorbent resins but are not always sufficient in effect. In many cases, an additive must be added in a large quantity or an additive exerting a very strong action must be used before the desired effect can be manifested. Under such circumstances, the essential physical properties or functions of the superabsorbent resin tend to be seriously ruined.

According to the inventors' study, it has turned out that the use of EDTA or sodium tripolyphosphate is not so effective in stabilizing a superabsorbent resin in the presence of an aqueous solution or water containing a radical generating species, e.g., hydrogen peroxide or L-ascorbic acid or a salt thereof.

In addition to the above-mentioned performance properties of superabsorbent resins, i.e., stability over time in a water-containing state (gel stability with time), the water absorption capacity (the amount of water absorbed), the rate of water absorption, the gel strength after swelling, liquid permeability, and the like are important requirements for superabsorbent resins. However, many of these properties conflict with each other, and it is very difficult to meet all of these requirements, which has been one of the problems in developing superabsorbent resins. For example, an attempt to increase water absorption capacity is generally accompanied by reductions in gel strength after swelling and liquid permeability.

In order to solve these problems, for example, Japanese Patent Laid-Open No. 36411/87 proposes graft-treating a carboxyl- and/or carboxylate-containing superabsorbent resin with a silane coupling agent. Japanese Patent Laid-Open No. 306118/94 proposes treating a superabsorbent resin with a titanium alkoxide. Nevertheless, these methods are still insufficient for satisfying both superabsorbent performance (e.g., a water absorption capacity) and gel stability with time after swelling.

Japanese Patent Laid-Open No. 145326/95 discloses the addition of a sulfate of a polyvalent metal selected from titanium, zirconium and vanadium to a superabsorbent polymer as one method for simultaneously improving gel strength, stability, and stickiness after water absorption.

According to the inventors' study, however, the gel stability over time achieved by this method is insufficient particularly for polymers having high water absorption capacity. Besides, addition of a polyvalent metal sulfate tends to reduce the initial rate of water absorption of the superabsorbent polymer or tends to make the polymer particles before water absorption ready to agglomerate due to the hygroscopicity of the polyvalent metal sulfate.

SUMMARY OF THE INVENTION

An object of the present invention is to provide a superabsorbent resin composition which exhibits high water absorption capacity and is yet stable against degradation and/or deterioration even in the presence of an aqueous solution or water containing a radical generating species, such as L-ascorbic acid or a salt thereof, or a transition metal ion, such as an iron ion or a copper ion.

The present invention provides a superabsorbent resin composition comprising following components (A), (B) and (C), or components (A) and (D):

(A) a superabsorbent resin,
(B) a metal compound containing at least one metal (referred to as metal A hereinafter) selected from the group consisting of titanium and zirconium,
(C) a chelating agent, and
(D) a coordination compound in which component (C) is coordinated with metal A.

The superabsorbent resin composition of the present invention is excellent in that it has high water absorption capacity and yet the superabsorbent resin used therein does not undergo degradation or deterioration even in the presence of an aqueous solution or water containing radical generating species, such as L-ascorbic acid or a salt thereof, or transition metal ions, such as iron or copper ions.

DESCRIPTION OF THE EMBODIMENT

The superabsorbent resin which can be used in the present invention as component (A) is not particularly limited and includes, for example, partially crosslinked polymers containing a carboxyl group or a salt thereof, such as a crosslinked polyacrylic acid salt, a crosslinked poly(vinyl alcohouacrylic acid salt) copolymer, a crosslinked starch-acrylic acid salt graft copolymer, and a crosslinked polyvinyl alcohol-polymaleic anhydride salt graft copolymer; and partially crosslinked polysaccharides, such as a crosslinked carboxymethyl cellulose salt. A crosslinked polyacrylic acid salt or a crosslinked starch-acrylic acid salt graft copolymer are preferred for their high water absorptivity. A crosslinked polyacrylic acid salt is the most preferred.

These superabsorbent polymers can be used either individually or as a combination of two or more thereof A "salt" of the superabsorbent resins illustrated above includes an alkali metal salt (e.g., sodium salt, potassium salt or lithium salt), an alkaline earth metal salt (e.g., calcium salt, magnesium salt or barium salt), and an ammonium salt (e.g., a quaternary ammonium salt or a quaternary alkylammonium salt).

The superabsorbent resin preferably has a degree of neutralization of 0.01 to 100%, still preferably 1 to 99%, particularly preferably 40 to 95%, based on the number of moles of the acid radical in the superabsorbent resin.

The terminology "degree of neutralization" as used herein denotes a molar ratio of acid radicals in a salt form to the total acid radicals of a superabsorbent resin, i.e., (the number of moles of acid radicals in salt form)/(the total number of moles of free acid radicals capable of forming a salt and acid radicals in salt form)×100 (%).

The metal compound which can be used in the present invention as component (B) is a compound containing at least one metal selected from the group consisting of titanium and zirconium (hereinafter referred to as metal A).

The metal compound as component (B) preferably includes the following compounds (B-1) to (B-6).
(B-1) Compounds obtained by mixing a hydroxy acid or a salt thereof with a polyvalent metal salt comprising at least one metal A selected from the group consisting of titanium and zirconium or an alkoxide of metal A.
(B-2) Compounds obtained by hydrolyzing a polyvalent metal salt comprising at least one metal A selected from the group consisting of titanium and zirconium or an alkoxide of metal A in the presence of a hydroxy acid or a salt thereof
(B-3) Titanium dioxide.
(B-4) Water-containing metal oxides comprising at least one metal A selected from the group consisting of titanium and zirconium and at least one metal selected from the group consisting of zinc, aluminum, calcium, magnesium, and silicon (hereinafter referred to as metal B).
(B-5) Titanium alkoxides.
(B-6) Sulfates of at least one metal A selected from the group consisting of titanium and zirconium.

Compound (B-1) is obtained by mixing a hydroxy acid or a salt thereof and a polyvalent metal salt comprising at least one metal A selected from the group consisting of titanium and zirconium or an alkoxide of metal A.

The hydroxy acid is a compound having a hydroxyl group and a carboxyl group per molecule and is not particularly limited in kind. Examples of suitable hydroxy acids are α-hydroxy acids. Where compound (B-2) is obtained by hydrolyzing component (B-1) as hereinafter described, it is desirable for the hydrolyzate be water-soluble. Accordingly, water-soluble hydroxy acids are preferred. Water-soluble α-hydroxy acids are still preferred. Examples of such α-hydroxy acids are gluconic acid, citric acid, isocitric acid, alloisocitric acid, lactic acid, hydroxyacetic acid, malic acid, and tartaric acid, with gluconic acid and citric acid being particularly preferred.

Examples of salts of the above-enumerated hydroxy acids include alkali metal salts (e.g., sodium salt, potassium salt, and lithium salts), alkaline earth metal salts (e.g., calcium salt, magnesium salt, and barium salt), and ammonium salts (e.g., quaternary ammonium salts and quaternary alkylammonium salts).

These hydroxy acids and salts thereof can be used either individually or as a mixture of two or more thereof The metal A is one or both of titanium and zirconium. In other words, titanium and zirconium can be used either alone or in combination. Titanium is preferred as metal A from the standpoint of the degree of improvement attained and economy.

The polyvalent metal salt made of metal A is not particularly limited and includes a sulfate, an oxysulfate, a chloride, an oxychloride, a nitrate, an oxynitrate, and a carboxylate of metal A. A sulfate, an oxysulfate, a chloride, and an oxychloride are preferred, with a sulfate and a chloride being still preferred.

The alkoxide of metal A includes a tetraisopropoxide and a tetrabutoxide of metal A.

When a hydroxy acid or a salt thereof and a polyvalent metal salt or polyvalent metal alkoxide are mixed, they are preferably mixed in the form of an aqueous solution or an alcoholic solution. In particular, where a polyvalent metal salt is used, they are preferably mixed in the form of an aqueous solution, and where a metal alkoxide is used, they are preferably mixed in the form of an alcoholic solution. When mixed as an aqueous solution or an alcoholic solution, the system provides a more effective compound.

The hydroxy acid or a salt thereof is preferably used in an amount of not less than twice the molar quantity of metal A in the polyvalent metal salt or alkoxide. If the molar ratio is less than 2, the system, i.e., a mixed solution, tends to become heterogeneous, which is unfavorable for the effects and handling properties discussed above.

It is preferable that the hydroxy acid or a salt thereof and the polyvalent metal salt or alkoxide be not only mixed but that the latter be hydrolyzed in the presence of the former. In this case, a more effective metal compound is obtained.

Compound (B-2) is a compound obtained by hydrolyzing a polyvalent metal salt comprising at least one metal A selected from the group consisting of titanium and zirconium or an alkoxide of metal A in the presence of a hydroxy acid or a salt thereof. That is, compound (B-2) is obtained by hydrolyzing compound (B-1). Therefore, the description about compound (B-1) hereinafter given will apply to compound (B-2) with respect to the kinds and amounts of the compounds used for obtaining compound (B-2) and the like.

Various techniques of hydrolysis can be employed. For example, a base, such as sodium hydroxide, potassium hydroxide, ammonia, amine, etc., is added, and, if necessary, the system is heated.

An illustrative example of the hydrolysis conditions is as follows. The base is preferably added in an amount 2 to 4 times the molar quantity of the metal A. The temperature of heating, if conducted, is preferably 60 to 100° C. The hydrolyzing time is preferably 20 to 60 minutes. Water, preferably ion-exchanged water, is used in an amount of 100 to 1000 parts by weight per 100 parts by weight of the polyvalent metal salt or polyvalent metal alkoxide.

It is preferable for the hydrolyzate, which contains compound (B-2), to be water-soluble. If the hydrolyzate has low water solubility and has a high insoluble content, the effects and handling properties are poor.

While the state of the resulting compound (B-1) or (B-2) on use in the preparation of a superabsorbent resin composition hereinafter described is not particularly limited, compound (B-1) is preferably used in the form of a solution as obtained by mixing in the form of an aqueous or alcoholic solution, and compound (B-2) is preferably used in the form of a metal compound solution as obtained by hydrolysis. The metal compound solution preferably has a metal A content of 0.05 to 5% by weight, particularly 0.2 to 2% by weight.

Titanium dioxide used as compound (B-3) is not particularly limited in shape and size but preferably has an average particle size of 0.1 $\mu$m or smaller, particularly 0.05 $\mu$m or smaller, especially 0.03 $\mu$m or smaller, and a specific surface area of 50 $m^2/g$ or more, particularly 100 $m^2/g$ or more, especially 200 $m^2/g$ or more, as measured by a Brunauer-Emmett-Teller method (hereinafter referred to as a BET specific surface area).

While the crystal form of titanium dioxide is not limited either, an anatase-type structure is preferred to a rutile-type structure for manifestation of higher effects of the present invention.

Compound (B-4) is a water-containing metal oxide comprising at least one metal A selected from the group consisting of titanium and zirconium and at least one metal B selected from the group consisting of zinc, aluminum, calcium, magnesium, and silicon. While not limiting, the water-containing metal oxide is preferably in a finely powdered state, being an aggregate of the water-containing metal oxide particles.

The terminology "water-containing metal oxide" as used herein means a hydrated oxide, that is, a hydrate of a metal oxide containing a hydroxide.

The water-containing metal oxide as compound (B-4) is a water-containing oxide containing a —$M^1$—O—$M^2$— bond (wherein $M^1$ is metal A, and $M^2$ is metal B) in at least part of its structure, which is different from a mere mixture of a water-containing oxide of $M^1$ and a water-containing oxide of $M^2$.

While any combination of metals A and B is effective, it is preferred from the standpoint of the degree of improvement attained and economy that titanium be used as metal A and zinc or aluminum, especially zinc, be used as metal B. In other words, a combination of titanium and zinc or a combination of titanium and aluminum is preferred.

The molar ratio of metal A to metal B in the water-containing metal oxide preferably ranges from 30/70 to 99/1, particularly 40/60 to 90/10. Out of the above molar ratio, the effect of combining metal A and metal B tends to be lessened.

It is preferred for the water-containing metal oxide to be amorphous as examined by X-ray diffractometry or the like crystal structure analytical methods. Amorphous water-containing metal oxide is more effective in suppressing degradation and deterioration of the superabsorbent resin even in a water-containing condition, i.e., in securing the stability of the superabsorbent resin with time.

The water-containing metal oxide can be obtained through various methods, such as a liquid phase method, a vapor phase method, and a solid phase method. From the standpoint of equipment and production cost, a liquid phase method, particularly a coprecipitation method is desirable. A coprecipitation method is generally a method in which two or more kinds of ions are precipitated simultaneously, i.e., coprecipitated. The coprecipitation method as referred to in the present invention is a method in which two or more kinds of ions in a mixed solution are coprecipitated by changing the concentration, pH, temperature, solvent, etc. of the mixed solution to obtain a coprecipitate having a prescribed composition, and the coprecipitate is separated and dried. Therefore, it is different from a method in which two or more kinds of metal ions are separately precipitated, collected, and dried, and the resulting precipitates are merely mixed together.

In the above coprecipitation method, coprecipitation can be induced by various techniques with no particularly restriction. For example, aqueous ammonia or urea is added to a mixed solution containing a salt of metal A and a salt of metal B while, if necessary, heating to cause coprecipitation.

The salt of metal A and that of metal B are not particularly limited. Useful salts of metal A or B include a sulfate, an oxysulfate, a chloride, an oxychloride, a nitrate, an oxynitrate, and a carboxylate, with a sulfate, an oxysulfate, a chloride, and an oxychloride being suited.

A coprecipitation method in which a metal A alkoxide and a metal B alkoxide in a mixed solution is hydrolyzed simultaneously is also suitable.

The alkoxide of metal A and that of metal B are not particularly limited and include, for example, a methoxide, an ethoxide, a propoxide and a butoxide of each metal.

The conditions causing coprecipitation are important, for they influence the rate of coprecipitation, the shape of the coprecipitate formed, and the like. Since the conditions vary depending on the starting material, the composition and concentration of the mixed solution, the kind of the coprecipitate, the method for causing coprecipitation, and the like, suitable conditions are to be selected according to these factors.

The coprecipitate thus obtained is filtered, washed, and dried. The drying temperature is preferably relatively low, for example, a range of from 100 to 200° C. being preferred. If the drying temperature exceeds 600° C., the stability of the superabsorbent resin with time will be diminished.

It is preferable for the water-containing metal oxide to have a large specific surface area. A preferred BET specific surface area is 100 $m^2/g$ or greater, particularly 200 $m^2/g$ or greater, for securing the stability of the superabsorbent resin with time.

The titanium alkoxide as compound (B-5) is not particularly limited as long as it is an organotitanium compound having a reactive alkoxy group. Suitable titanium alkoxides include titanium tetramethoxide, titanium tetraethoxide, titanium tetraisopropoxide, titanium tetrabutoxide, titanium tetrastearyloxide, titanium tetrakis(2-ethylhexyloxide), a titanium tetraisopropoxide polymer, a titanium tetrabutoxide polymer, diisopropoxybis(acetylacetonato)titanium, dibutoxybis(triethanolaminato)titanium, titanium tributoxide stearate, and titanium diisopropoxide distearate.

The sulfate of at least one metal A selected from the group consisting of titanium and zirconium as compound (B-6) includes titanium sulfate, titanyl sulfate, and zirconium sulfate.

The metal compound as component (B) preferably has a metal A content of 0.001 to 1 part by weight, particularly 0.005 to 0.5 part by weight, especially 0.01 to 0.1 part by weight, per 100 parts by weight of a superabsorbent resin as component (A).

If the metal A content is less than 0.001 part by weight, the resulting resin composition has insufficient gel stability. Even if the metal A content exceeds 1 part by weight, a further improvement is little expected.

The "superabsorbent resin" as referred to as a basis of contents is intended to mean a superabsorbent resin in its water-free dry state.

The chelating agent as component (C) is a chelating agent having a metal chelating ability, i.e., a compound having a bidentate or polydentate ligand capable of bonding to a metal ion to form a metal chelate. It should be noted, however, that when compound (B-1) or (B-2) is used as component (B), a hydroxy acid or a salt thereof is excluded from the chelating agent (component (C)).

Specific but non-limiting examples of the chelating agent as component (C) include water-soluble inorganic phosphoric acid compounds, such as polyphosphoric acids, e.g., tripolyphosphoric acid, tetrapolyphosphoric acid, pentapolyphosphoric acid, pyrophosphoric acid, metaphosphoric acid, and polyphosphoric acid and salts thereof (e.g., Na salt or K salt); aminocarboxylic acid compounds, such as ethylenediaminetetraacetic acid, 1,3-propanediaminetetraacetic acid, diethylenetriaminepentaacetic acid, triethylenetetraminehexaacetic acid, L-glutamic acid diacetic acid, N,N-Bis(carboxymethyl)-L-glutamic acid, and hydroxyethylethylenediaminetriacetic acid, and salts thereof (e.g., Na, K or ammonium salt); polyhydroxy compounds, such as glycol and glycerol; amine compounds, such as ethylenediamine, 1,10-phenanthroline, 2,2'-bipyridine, and terpyridine; dicarboxylic acid compounds, such as oxalic acid or its salts (e.g., Na, K or ammonium salt); organic phosphorus compounds, such as aminotri(methylenephosphonic acid), 1-hydroxyethylidene-1,1-diphosphonic acid, ethylenediaminetetra(methylenephosphonic acid), diethylenetriaminepenta(methylenephosphonic acid), and 2-phosphonobutane-1,2,4-tricarboxylic acid, and salts thereof(e.g., Na, K or ammonium salt); tropolone or derivatives thereof, such as β-thujaplicin, γ-thujaplicin, and salts thereof (e.g., Na, K or ammonium salt); compounds serving as a surface active agent, such as compound represented by formula (I):

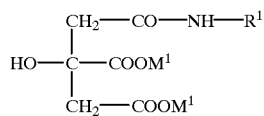

(I)

wherein $R^1$ represents an alkyl or alkenyl group having 6 to 30 carbon atoms; and $M^1$'s, which may be the same or different, each represents an alkali metal ion, an ammonium ion or a hydrogen atom, such as a citric monoalkylamide and a citric monoalkenylamide; compounds represented by formula (II):

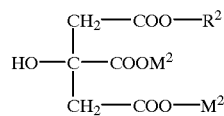

(II)

wherein $R^2$ represents an alkyl or alkenyl group having 6 to 30 carbon atoms; and $M^2$'s, which may be the same or different, each represent an alkali metal ion, an ammonium ion or a hydrogen atom, such as a monoalkyl citrate or a monoalkenyl citrate; compounds represented by formula (III):

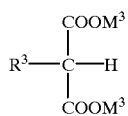

(III)

wherein $R^3$ represents an alkyl or alkenyl group having 6 to 30 carbon atoms; and $M^3$'s, which may be the same or different, each represent an alkali metal ion, an ammonium ion or a hydrogen atom, such as an alkylmalonic acid and an alkenylmalonic acid; compounds represented by formula (IV):

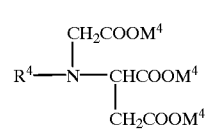

(IV)

wherein $R^4$ represents an alkyl or alkenyl group having 6 to 30 carbon atoms; and $M^4$'s, which may be the same or different, each represent an alkali metal ion, an ammonium ion or a hydrogen atom, such as an N-alkyl-N'-carboxymethylaspartic acid and an N-alkenyl-N'-carboxymethylaspartic acid; compounds represented by formula (V):

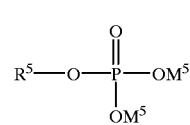

(V)

wherein $R^5$ represents an alkyl or alkenyl group having 6 to 30 carbon atoms; and $M^5$'s, which may be the same or different, each represent an alkali metal ion, an ammonium ion or a hydrogen atom, such as a monoalkyl phosphate and a monoalkenyl phosphate; compounds presented by formula (VI):

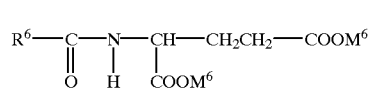

(VI)

wherein $R^6$—CO— represents an acyl group having 6 to 30 carbon atoms; and $M^6$'s, which may be the same or different, each represent an alkali metal ion, an ammonium ion, a triethanolammonium ion or a hydrogen atom, such as an N-acylated glutamic acid; and compounds represented by formula (VII):

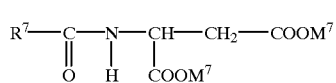

(VII)

wherein $R^7$—CO— represents an acyl group having 6 to 30 carbon atoms; and $M^7$'s, which may be the same or different, each represent an alkali metal ion, an ammonium ion, a triethanolammonium ion or a hydrogen atom, such as an N-acylated aspartic acid; and β-diketone compounds, such as acetylacetone, 4-hydroxybenzoylacetone and 4-hydroxybenzoylmethane-t-butyl ketone. Among them preferred are water-soluble inorganic phosphoric acid compounds, aminocarboxylic acid compounds, organic phosphorus compounds, and surface active agent compounds. Particularly preferred are tripolyphosphoric acid, polyphosphoric acid, ethylenediaminetetraacetic acid, 1-hyhdroxyethylidene- 1,1-diphosphonic acid, monoalkyl phosphates, 2-phosphonobutane-1,2,4-tricarboxylic acid, L-glutamic acid diacetic acid, N,N-Bis(carboxymethyl)-L-glutamic acid, hydroxyethylethylenediaminetriacetic acid, or salts thereof (e.g., Na, K or ammonium salt).

Where a metal compound as component (B) is selected from compound (B-3), compound (B-4), compound (B-5)

and compound (B-6), the chelating agent as component (C) further includes oxycarboxylic acid compounds, such as tartaric acid, gluconic acid, citric acid, salicylic acid or salts thereof (e.g., Na, K or ammonium salt).

The chelating agent as component (C) is preferably used in an amount of 0.01 to 5 parts by weight, particularly 0.05 to 2 parts by weight, per 100 parts by weight of a superabsorbent resin as component (A).

If the content of the chelating agent is less than 0.01 part by weight, the resulting resin composition has insufficient gel stability. Even if the content of the chelating agent exceeds 5 parts by weight, a further improvement is little expected.

From the viewpoint of stability with time in the presence of water in which radical generating species such as L-ascorbic acid or salt are dissolved, component (C)/metal A is preferably 0.8–10, more preferably 1.5–5 in terms of molar ratio.

Component (C) may be coordinated with metal A in the present invention. The compound (metal chelate compound) in which component (C) is coordinated with metal A is referred to component (D) here.

The content of component (D) based on component (A) is preferably the total of preferable contents of metal A and component (C).

The superabsorbent resin composition of the present invention can contain water in addition to the superabsorbent resin as component (A), the metal compound as component (B), and the chelating agent as component (C), or the superabsorbent resin as component (A) and the metal chelate compound as component (D). This case includes an embodiment in which the superabsorbent resin is a water-containing polymer and an embodiment in which the composition is in a water-containing gel state. The superabsorbent resin composition can contain water within its absorptive capacity.

If desired, the superabsorbent resin composition can contain various additives, such as a water-soluble organic solvent, a surface active agent, a salt, inorganic fine particles, a stabilizer, an antioxidant, a reducing agent and/or an antiseptic. Water and these additives can be added in a total amount of not more than 50% by weight based on the total weight superabsorbent resin composition.

A process for producing the superabsorbent resin composition which comprises mixing (A) the superabsorbent resin, B) the metal compound containing at least one metal A selected from the group consisting of titanium and zirconium, and (C) the chelating agent, or mixing (A) the superabsorbent resin and (D) a coordination compound in which component (C) is coordinated with metal A. The following methods (1) to (3) are given as examples. (1) A method comprising previously adding the metal compound and the chelating agent to the preparation system of the superabsorbent resin. For example, in using a water-soluble vinyl monomer for providing a superabsorbent resin, the metal compound and the chelating agent are previously mixed with the water-soluble vinyl monomer, and the monomer is polymerized. (2) A method comprising spraying an aqueous solution containing the metal compound and the chelating agent onto the superabsorbent resin either in a dry state or a water-containing condition and, if desired, drying the resin.
(3) A method comprising dry mixing the superabsorbent resin with the metal compound and the chelating agent, both in a dry state.

In carrying out the above methods, the metal compound and the chelating agent may be mixed together beforehand and added to the superabsorbent resin (or the preparation system thereof) or be separately added. Further, the metal compound and the chelating agent may be added by the same method or different methods selected from the methods (1) to (3).

While the water absorption capacity of the superabsorbent resin composition according to the present invention is not particularly limited, it is preferable for the composition to have a water holding power of 35 g/g or more, particularly 38 g/g or more, as measured in accordance with a holding power measuring method by centrifugal dehydration hereinafter described.

In general, as the water absorption capacity of the superabsorbent resin composition increases, the amount of resin required per article, e.g., diaper, decreases, which contributes to reductions in the thickness of the diaper and manufacturing cost. However, as the water absorption capacity increases, the performance properties, such as gel stability over time, gel strength, and liquid permeability, are generally reduced. Therefore, resins exhibiting super absorptivity are difficult to apply to disposable diapers. To the contrary, the superabsorbent resin composition according to the present invention has a relatively high water absorption capacity having a holding power of 35 g/g or more and yet hardly undergoes such reductions in performance.

As stated above, the superabsorbent resin composition of the present invention is particularly useful as a water-absorbing material in sanitary articles, such as absorbent articles, e.g., disposable diapers and sanitary napkins. Such absorbent articles comprise a water-permeable topsheet, a water-impermeable backsheet and an absorbent member interposed between said topsheet and said backsheet. The absorbent member can be made up of fluff pulp, i.e., ground wood pulp. The superabsorbent resin composition of the present invention is used in combination with the fluff pulp either as a mixture with the fluff pulp or in the form of an independent layer on specific areas of a fluff pulp layer. The absorbent member can be prepared by heat treating a mixture of a thermoplastic resin, fluff pulp, and the superabsorbent resin composition of the present invention.

As mentioned above, because body fluids such as urine contain L-ascorbic acid or a salt thereof superabsorbent resin in a conventional superabsorbent resin composition deteriorates by such substances present in body fluids absorbed by the absorbent articles. To the contrary, where the superabsorbent resin composition of the present invention is used as a water-absorbing material of absorbent articles, deterioration of the superabsorbent resin can be suppressed.

Moreover, the superabsorbent resin composition of the present invention has high gel strength and high liquid permeability after swelling, and is therefore suitable for use in absorbent articles, such as disposable diapers and sanitary napkins.

Unless otherwise indicated, all the percents and parts in the following Examples and Comparative Examples are given by weight.

The test methods used in the Examples and Comparative Examples are described below.
1) Measurement of Holding Power by Centrifugal Dehydration Method A superabsorbent resin composition weighing 1 g was swollen with 150 ml of physiological saline (0.9% NaCl solution, produced by Otsuka Pharmaceutical Co., Ltd.) for 30 minutes and put in a bag made of nonwoven fabric. The bag and the contents were dehydrated in a centrifugal separator at 143 G for 10 minutes and weighed (overall weight). The holding power after centrifugal dehydration was calculated according to equation (1).

Holding power after centrifugal dehydration (g/g)=[(overall weight)−(weight of nonwoven fabric bag)−(weight of superabsorbent resin composition)−(residue of liquid in nonwoven fabric bag)]/(weight of superabsorbent resin composition)  (1)

2) Evaluation of Gel Stability with Time after Swelling:

A superabsorbent resin composition weighing 1 g was swollen with 45 g of physiological saline containing 0.05% of L-ascorbic acid. The swollen resin composition was sealed in a screw tube and allowed to stand at 40° C. for 3 hours. The state of the swollen gel after the standing was observed by the eye to evaluate the gel stability with time. The evaluation on gel stability with time was made in terms of gel flowability, stringiness, and shape retention according to a 4-grade rating system shown in Table 1 below. Gel flowability was observed by tilting the screw tube up, stringiness was observed by stirring the gel with spatula, and shape retention was observed by the eye after taking out of the screw tube. If the gel has flowability and stringiness, it means that the superabsorbent resin is degraded. If the degree of shape retention lowers, it means that the superabsorbent resin is degraded. Superabsorbent resin compositions graded A or B are to be suitable for use as a water-absorbing material in sanitary napkins, disposable diapers, sheets for adults, tampons, absorbent cotton, etc.

TABLE 1

| Grade | Flowability | Stringiness | Shape Retention |
| --- | --- | --- | --- |
| A | non-flowable | non-stringy | unchanged |
| B | Slightly Flowable | Slightly Stringy | slightly changed |
| C | Flowable | Stringy | partly liquefied |
| D | Flowable | Stringy | largely liquefied |

Synthesis Examples for the superabsorbent resins, metal compounds and metal chelate compound used in Examples and Comparative Examples are shown below. All the metal compounds and metal chelate compound in Synthesis Examples were obtained in the form of a solution.

SYNTHESIS EXAMPLE 1

Synthesis of Superabsorbent Resins (1) and (2)

In a 1000 ml four-necked flask equipped with a stirrer, a reflux condenser, a dropping funnel, and a tube for nitrogen gas introduction were charged 400 ml of cyclohexane and 0.625 g (0.5% based on the produced polymer) of ethyl cellulose (Ethyl Cellulose N-100, produced by Hercules Powder Co.) as a dispersant. Nitrogen gas was blown into the mixture to driven out dissolved oxygen, and the contents of the flask were kept at 75° C.

In a separate flask 102.0 g of acrylic acid was diluted with 25.5 g of ion-exchanged water, and the solution was neutralized with 140 g of a 30% sodium hydroxide aqueous solution while cooling from outside. To the aqueous solution was added a solution of 0.204 g (0.2% based on the acrylic acid) of potassium persulfate in 7.5 g of water. Nitrogen gas was blown into the solution to remove dissolved oxygen. The contents of the flask were put dropwise into the above four-necked flask over 1 hour to carry out polymerization. After completion of the polymerization, the reaction mixture was azeotropically dehydrated by the use of a dehydrating tube so as to adjust the water content of the resulting superabsorbent resin to 30 parts per 100 parts of the resin. Then a solution of 0.04 g (0.04% based on the acrylic acid) of polyglycerol polyglycidyl ether (Denacol EX-512, produced by Nagase Kasei Kogyo K.K.) in 4 g of water was added thereto as a crosslinking agent, followed by allowing the mixture to react at 75 to 80° C. for 1 hour. After cooling, cyclohexane was removed by decantation to collect the superabsorbent resin (water-containing), which is designated superabsorbent resin (1).

The superabsorbent resin (1) was dried at 80 to 100° C. under reduced pressure of 50 Torr. The resulting resin is designated superabsorbent resin (2).

SYNTHESIS EXAMPLE 2

Synthesis of Superabsorbent Resins (3) and (4)

A water-containing superabsorbent resin, designated superabsorbent resin (3), was prepared in the same manner as in Synthesis Example 1, except for replacing the ethyl cellulose used as a dispersant with 1.5 g of a 25% aqueous solution of sodium polyoxyethylene lauryl ether sulfate (average mole number of ethylene oxide added =2) and increasing the amount of the polyglycerol polyglycidyl ether used as a crosslinking agent from 0.04 g to 0.06 g.

The superabsorbent resin (3) was dried at 80 to 100° C. under reduced pressure of 50 Torr. The resulting resin is designated superabsorbent resin (4).

SYNTHESIS EXAMPLE 3

Synthesis of Metal Compound (5)

To an ice-cooled solution of 43.6 g of sodium gluconate in 150 g of ion-exchanged water was added dropwise 20 g of titanium tetrachloride and mixed. After confirming that the solution turned clear, about 48 g of a 30% sodium hydroxide aqueous solution was added thereto dropwise to adjust the solution to pH 7. The resulting solution was clear and faintly yellow and had a titanium content of 1.9% (calculated).

SYNTHESIS EXAMPLE 4

Synthesis of Metal Compound (6)

To 50 g of a titanium oxysulfate solution having a titanium content of 4.9% (Titanyl Sulfate Solution, produced by Kisan Kinzoku K. K.) were added 32.2 g of citric acid monohydrate and 25 g of ion-exchanged water and mixed. After confirming that citric acid completely dissolved, about 104 g of a 30% sodium hydroxide aqueous solution was added thereto dropwise while cooling from outside to adjust the solution to pH 7. The resulting solution was yellow and slightly turbid. The titanium content of the solution was 1.2% (calculated).

SYNTHESIS EXAMPLE 5

Synthesis of Metal Compound (7)

A solution of 23.3 g of titanium tetrachloride ($TiCl_4$) in 51 ml of water and a solution of 20 g of zinc chloride ($ZnCl_2$) in 100 ml of water were mixed, and the mixture was diluted with water to make 5 liters. To the mixed solution was added 71.5 g of urea, followed by stirring. The solution had a pH of 2. On heating the solution at 95° C. for 20 minutes, a white coprecipitate was gradually formed. The heating was continued until the pH of the solution rose to 7. The coprecipitate was collected by filtration and dried at 120° C. for 3 hours to obtain fine powder comprising water-containing metal oxide aggregates, which is designated metal compound (7).

The metal compound (7) had a BET specific surface area of 250 m²/g and a Ti/Zn molar ratio of 46:54.

SYNTHESIS EXAMPLE 6

Synthesis of Metal Compound (8)

To a solution of 34.0 g of zirconium oxychloride octahydrate in 150 g of ion-exchanged water was added 43.6 g of sodium gluconate and dissolved. About 22 g of a 30% sodium hydroxide aqueous solution was added thereto dropwise to adjust the solution to pH 7. The resulting solution was clear and faintly yellow and had a zirconium content of 3.86% (calculated).

SYNTHESIS EXAMPLE 7

Synthesis of Metal Chelate Compound (9)

To 29.3 g of a titanium oxysulfate solution having a titanium content of 4.9% was added 23.0 g of a 50% citric acid aqueous solution (produced by Fuso Kagaku Kogyo K. K.) and mixed. To the aqueous solution was added 20.6 g of a 60% of 1-hydroxyethylidene-1,1-diphosphonic acid aqueous solution (Dequest 2010CS, produced by Nippon Monsanto K. K.) and mixed. While cooling the mixture outside, 27 g of a 30% sodium hydroxide aqueous solution was added thereto dropwise to adjust the solution to pH 7. The resulting solution was pale yellow and slightly turbid. The titanium content of the solution was 1.5% and the 1-hydroxyethylidene-1,1-diphosphonic acid content was 13.4%. To 2.4 g of the resulting solution was added 1.6 g of heavy water, followed by the measurement of $^{13}$C-NMR with the use of Varian UNITY INOVA 300MB. The results evidenced that the peak of 72 ppm of the carbon atom located at 1-position of 1-hydroxyethylidene-1,1-diphosphonic acid was split into 68 to 72 ppm, and the peak of 20 ppm of the methyl group was split to 18 ppm, and the 1-hydroxyethylidene- 1,1-diphosphonic acid was coordinated with titan.

EXAMPLES 1 TO 10

The superabsorbent resin (A) shown in Table 2 below was put in a twin-cylinder kneader, and the metal compound (B) shown in Table 2 and the chelating agent (C) shown in Table 2 were added thereto in amounts shown (per 100 parts of the superabsorbent resin) either in a powder form or by spraying an aqueous solution thereof. The mixture was thoroughly stirred to mix to obtain a superabsorbent resin composition. The amount of the metal compound (B) is in terms of metal A content.

Where superabsorbent resin (1) or (3) was used, the mixture was dried at 80 to 100° C. under reduced pressure of 50 Torr to obtain a superabsorbent resin composition. The resulting resin composition was evaluated in terms of water holding power after centrifugal dehydration and stability of swollen gel according to the above-described testing methods. The results obtained are shown in Table 2.

Before making evaluation, coarse particles of 850 μm or greater were removed from the composition by sieving. The same evaluation was repeated in the following Example 11 and Comparative Examples 1–5.

EXAMPLE 11

The superabsorbent resin (1) was put in a twin-cylinder kneader, and the metal chelate compound (9) (14.9% aqueous solution) obtained in Synthesis Example 7 as component (D) was added thereto by spraying, such that the Ti content was 0.03 parts based on 100 parts of the superabsorbent resin. Then, the same procedure as that of Example 1 was repeated to obtain a superabsorbent resin composition, and the same evaluation was repeated. The evaluation results show that the holding power after centrifugal dehydration was 43 g/g, and the stability of the swollen gel was graded A.

Comparative Examples 1 and 2

The superabsorbent resin (A) alone shown in Table 3 below was tested in the same manner as in Example 1, with neither a metal compound as component (B) nor a chelating agent as component (C) being added thereto. The results obtained are shown in Table 3.

Comparative Examples 3 TO 5

The superabsorbent resin (3) as component (A) was mixed with either one of a metal compound as component (B) and a chelating agent as component (C) as shown in Table 3 to prepare a superabsorbent resin composition in the same manner as in Examples. Similarly to Examples, the superabsorbent resin composition was dried at 80 to 100° C. under reduced pressure of 50 Torr and tested in the same manner as in Examples. The results obtained are shown in Table 3.

*1,*2 and *3 in the following Tables 2 and 3 are as follows:

*1: Content of metal A (Ti or Zr) per 100 parts the superabsorbent resin (A).

*2: Titanium dioxide produced by Ishihara Sangyo, Kaisha (anatase type; average particle size: 7 nm; BET specific surface area: 320 m²/g)

*3: Titanium dioxide produced by Ishihara Sangyo, Kaisha (rutile type; average particle size: 40 nm; BET specific surface area: 40 m²/g)

TABLE 2

| Example No. | Super-absorbent Resin (A) | Metal Compound (B) | | | Chelating Agent (C) | | | Performance Properties | |
|---|---|---|---|---|---|---|---|---|---|
| | | Kind | Metal A Content (part*¹) | Method of Addition | Kind | Amount (part) | Method of Addition | Holding Power (g/g) | Swollen Gel Stability |
| 1 | (1) | (5) | 0.03 | Sprayed | Na tripoly-phosphate | 0.5 | 10% soln. sprayed | 43 | A |
| 2 | (1) | (5) | 0.03 | Sprayed | Monoalkyl phosphate (C₁₂) | 0.5 | 4% soln. sprayed | 43 | A |

TABLE 2-continued

| Example No. | Super-absorbent Resin (A) | Metal Compound (B) | | | Chelating Agent (C) | | | Performance Properties | |
|---|---|---|---|---|---|---|---|---|---|
| | | Kind | Metal A Content (part*1) | Method of Addition | Kind | Amount (part) | Method of Addition | Holding Power (g/g) | Swollen Gel Stability |
| 3 | (1) | (6) | 0.04 | Sprayed | Na 1-hydroxy ethylidene-1,1-diphosphonate | 0.5 | 30% soln. sprayed | 45 | A |
| 4 | (2) | ST-01*2 | 0.4 | Added as powder | Monoalkyl phosphate ($C_{12}$) | 0.5 | added as powder | 42 | A |
| 5 | (3) | TTO-55(N)*3 | 0.6 | Added as powder | Na tripolyphosphate | 1.0 | 10% soln. sprayed | 43 | B |
| 6 | (3) | (7) | 0.1 | Added as powder | Na 1-hydroxy-ethylidene-1,1-diphosphonate | 0.5 | 30% soln. sprayed | 44 | A |
| 7 | (3) | Titanium tetraiso-propoxide | 0.1 | Sprayed | Na 1-hydroxy-ethylidene-1,1-diphosphonate | 0.5 | 30% soln. sprayed | 40 | A |
| 8 | (3) | Titanyl sulfate | 0.04 | Sprayed | Na tripolyphosphate | 1.5 | 10% soln. Sprayed | 42 | A |
| 9 | (4) | (7) | 0.2 | Added as powder | 2Na ethylenedi-aminetetraacetate | 0.5 | Added as powder | 43 | A |
| 10 | (1) | (8) | 0.04 | Sprayed | Na 1-hydroxy-ethylidene-1,1-diphosphonate | 0.5 | 30% soln. sprayed | 43 | A |

TABLE 3

| Compara. Example No. | Super-absorbent Resin (A) | Metal Compound (B) | | | Chelating Agent (C) | | | Performance Properties | |
|---|---|---|---|---|---|---|---|---|---|
| | | Kind | Metal A Content (part*1) | Method of Addition | Kind | Amount (part) | Method of Addition | Holding Power (g/g) | Swollen Gel Stability |
| 1 | (2) | — | — | — | — | — | — | 43 | C |
| 2 | (4) | — | — | — | — | — | — | 47 | D |
| 3 | (3) | titanium tetraiso—propoxide | 0.1 | Sprayed | — | — | — | 41 | C |
| 4 | (3) | titanyl sulfate | 0.04 | Sprayed | — | — | — | 44 | C |
| 5 | (3) | — | — | — | Na tripolyphosphate | 1.0 | 10% soln. Sprayed | 44 | D |

As is apparent from the results in Tables 2 in view of Table 3, the superabsorbent resin compositions according to the present invention (Examples 1 to 11) which comprise components (A), (B) and (C), or components (A) and (D) are superior to the comparative compositions in both holding power after centrifugal dehydration and stability of swollen gel.

What is claimed is:

1. A superabsorbent resin composition comprising the following components (A), (B) and (C):
   (A) a superabsorbent resin,
   (B) a metal compound containing at least one metal A selected from the group consisting of titanium and zirconium, and
   (C) a chelating agent in an amount of 0.01 to 5 parts by weight of said component (A), wherein said chelating agent is selected from the group consisting of tripoly-phosphoric acid, polyphosphoric acid, ethylenedi-aminetetraacetic acid, 1-hydroxyethylidene-1,1-diphosphonic acid, a monoalkyl phosphate and salts thereof.

2. The superabsorbent resin composition according to claim 1, wherein said metal compound as component (B) is a compound obtained by mixing a hydroxy acid or a salt thereof with a polyvalent metal salt comprising at least one metal A selected from the group consisting of titanium and zirconium or an alkoxide of said metal A.

3. The superabsorbent resin composition according to claim 1, wherein said metal compound as component (B) is obtained by hydrolyzing a polyvalent metal salt comprising at least one metal A or an alkoxide of said metal A, in the presence of a hydroxy acid or a salt thereof, wherein said metal A is selected from the group consisting of titanium and zirconium.

4. The superabsorbent resin composition according to claim 1, wherein said metal compound as component (B) is a water-containing metal oxide comprising at least one metal A selected from the group consisting of titanium and zirconium and at least one meatl B selected from the group consisting of zinc, aluminum, calcium, magnesium, and silicon.

5. The superabsorbent resin composition according to claim 1, which is capable of holding 35 g/g or more of physiological saline after being swollen with physiological saline for 30 minutes and dehydrated by centrifugation.

6. A process for producing the superabsorbent resin composition as claimed in claim 1, comprising the step of mixing together:

(A) the superabsorbent resin,
(B) the metal compound containing at least one metal A selected from the group consisting of titanium and zirconium, and
(C) the chelating agent.

* * * * *